(12) United States Patent
Forman et al.

(10) Patent No.: US 11,172,842 B2
(45) Date of Patent: Nov. 16, 2021

(54) METHOD AND DEVICE FOR ANALYZING ACQUIRED MAGNETIC RESONANCE IMAGES

(71) Applicant: Siemens Healthcare GmbH, Erlangen (DE)

(72) Inventors: Christoph Forman, Erlangen (DE); Andreas Greiser, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 131 days.

(21) Appl. No.: 16/520,699

(22) Filed: Jul. 24, 2019

(65) Prior Publication Data

US 2020/0029853 A1 Jan. 30, 2020

(30) Foreign Application Priority Data

Jul. 24, 2018 (EP) .................................... 18185260

(51) Int. Cl.
*A61B 5/055* (2006.01)
*G01R 33/56* (2006.01)
*G06T 7/00* (2017.01)
*G06T 7/10* (2017.01)
*G01R 33/561* (2006.01)
(Continued)

(52) U.S. Cl.
CPC .......... *A61B 5/055* (2013.01); *G01R 33/5608* (2013.01); *G06T 7/0012* (2013.01); *A61B 5/742* (2013.01); *G01R 33/561* (2013.01); *G01R 33/565* (2013.01); *G06T 7/10* (2017.01); *G06T 2207/10088* (2013.01)

(58) Field of Classification Search
CPC .............. G01R 33/5608; G01R 33/561; G01R 33/565; G06T 7/0012; G06T 7/10; G06T 2207/10088
See application file for complete search history.

(56) References Cited

U.S. PATENT DOCUMENTS

| 2006/0197525 A1* | 9/2006 | Mens | G01R 33/565 324/307 |
| 2014/0081125 A1* | 3/2014 | Zhou | A61B 5/055 600/419 |
| 2017/0273577 A1* | 9/2017 | Miyazaki | G06T 7/0016 |

OTHER PUBLICATIONS

Salerno Michael et al.; "Advances in Parametric Mapping With CMR Imaging"; JACC: Cardiovascular Imaging; vol. 6; No. 7; Jul. 8, 2013 (Jul. 8, 2013); pp. 806-822, XP028672138; ISSN: 1936-878X; DOI: 10.1016/J.JCMG.2013.05.005; 2013.

(Continued)

*Primary Examiner* — Gregory H Curran
(74) *Attorney, Agent, or Firm* — Schiff Hardin LLP

(57) ABSTRACT

In a method for analyzing acquired magnetic resonance images, an image series is provided that includes acquired magnetic resonance images of a slice of an object, picture elements of the acquired magnetic resonance images of the image series are fitted to generate a parameter map and an error map, the acquired magnetic resonance images are automatically segmented to generate image segments, histograms of the parameter map and the error map are generated based on the image segments, and the histograms are analyzed to generate an output of analysis results and/or generate a visualization including the parameter map, the error map, and the image segments. The acquired magnetic resonance images can have a variation of a contrast-determining acquisition parameter.

19 Claims, 5 Drawing Sheets

(51) Int. Cl.
A61B 5/00 (2006.01)
G01R 33/565 (2006.01)

(56) References Cited

OTHER PUBLICATIONS

Christopher M Sandino et al.; "Myocardial T2* mapping: influence of noise on accuracy and precision"; Journal of Cardiovascular Magnetic Resonance; Biomed Central LTD; London UK; vol. 17; No. 1; Feb. 4, 2015 (Feb. 4, 2015); p. 7; XP021213192; ISSN: 1532-429X; DOI: 10.1186/S12968-015-0115-3; 2015.

Silva Samuel et al.; "Myocardial Perfusion Analysis from Adenosine-Induced Stress MDCT"; Jun. 8, 2011 (Jun. 8, 2011); International Conference on Simulation; Modeling; and Programming for Autonomous Robots; SIMPAR 2010; [Lecture Notes in Computer Science; Lect.Notes Computer]; Springer; Berlin; Heidelberg; pp. 717-725; XP047427250; ISBN: 978-3-642-17318-9; 2011.

Peter Kellman et al.; "T1 and extracellular volume mapping in the heart: estimation of error maps and the influence of noise on precision"; Journal of Cardiovascular Magnetic Resonance; Biomed Central LTD; London UK; vol. 15; No. 1; Jun. 21, 2013 (Jun. 21, 2013); p. 56; XP021155538; ISSN: 1532-429X; DOI:10.1186/1532-429X-15-56; 2013.

Huelnhagen Till et al.; "High Spatial Resolution Myocardial T2* Mapping at 7.0 T Reveals Differences Between Healthy Volunteers and Patients With Hypertrophic Cardiomyopathy"; International Society for Magnetic Resonance in Medicine,; ISMRM; 2030 Addison Street, 7th Floor, Berkeley, CA 94704 USA; vol. 23; May 15, 2015 (May 15, 2015); p. 2599; XP040668276; 2015.

Bettina Baessler et al.; "Mapping tissue inhomogeneity in acute myocarditis: a novel analytical approach to quantitative myocardial edema imaging by T2-mapping"; Journal of Cardiovascular Magnetic Resonance; vol. 17; No. 1; Dec. 1, 2015 (Dec. 1, 2015); pp. 1-11; XP055525806; DOI: 10.1186/sl2968-015-0217-y; 2015.

European Action dated Dec. 4, 2018, for application No. 18185260.9.

M. Ugander et al., "Myocardial ECV imaging by MRI compared to myocardial ECV imaging by CT—validation in experimental acute myocardial infarction", Proc. Intl. Soc. Mag. Reson. Med. 19 (2011), p. 1369.

* cited by examiner

FIG 3
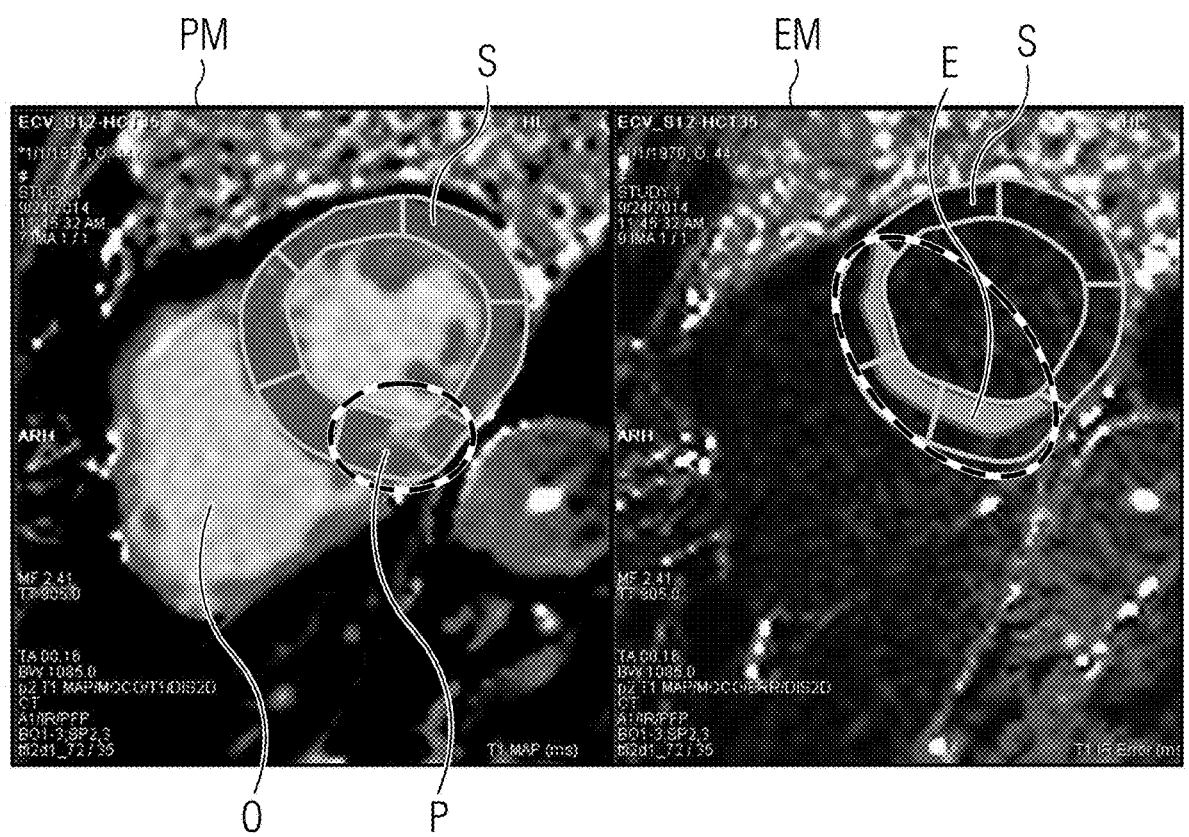
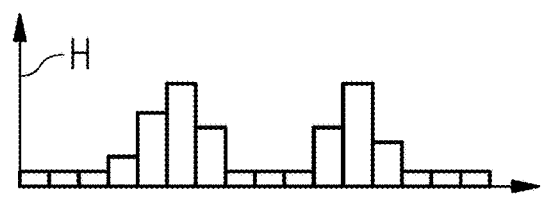
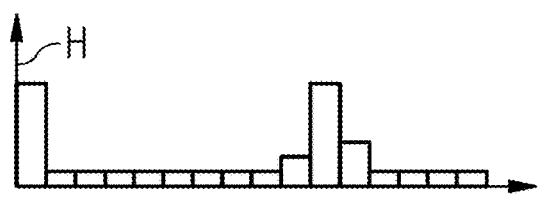

FIG 4
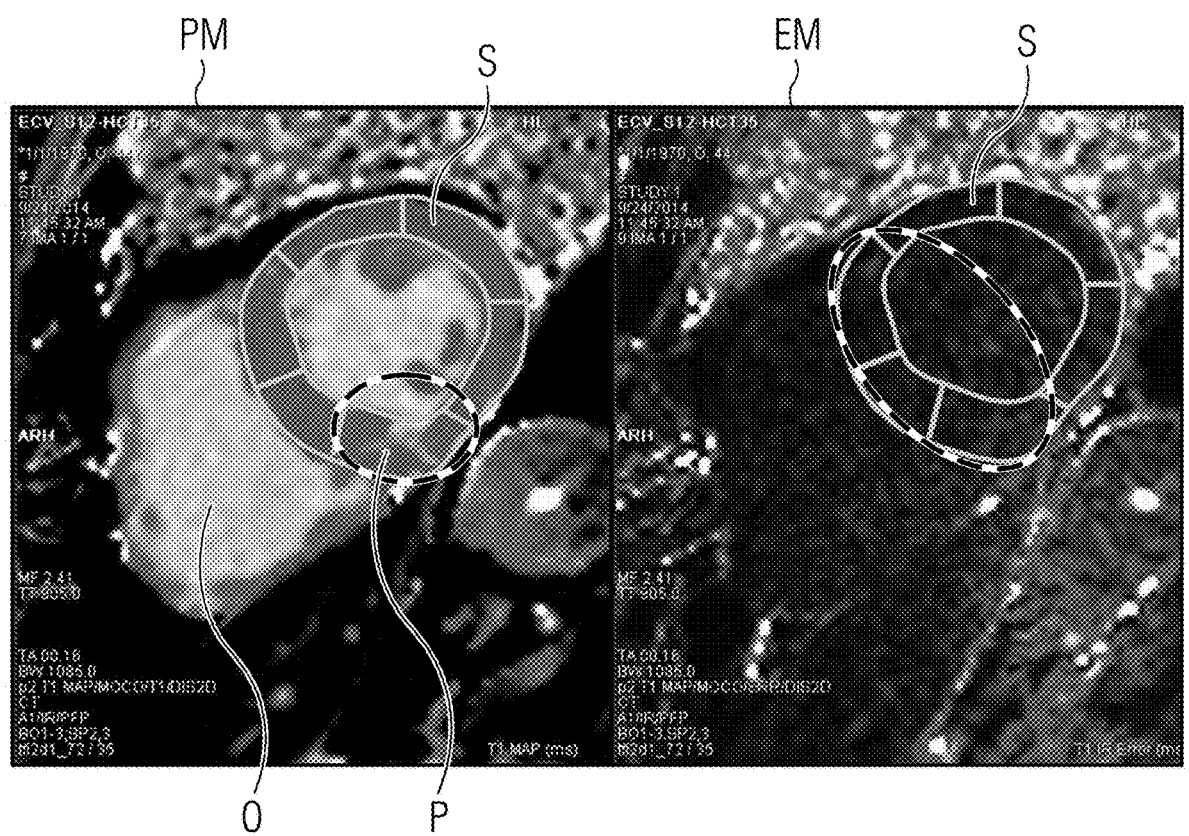
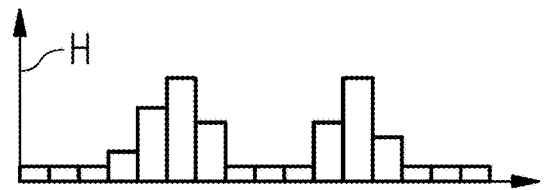
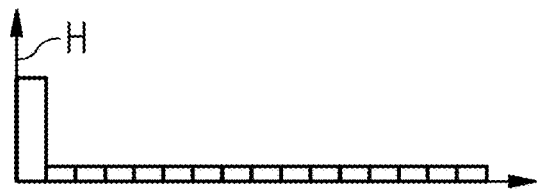

FIG 5
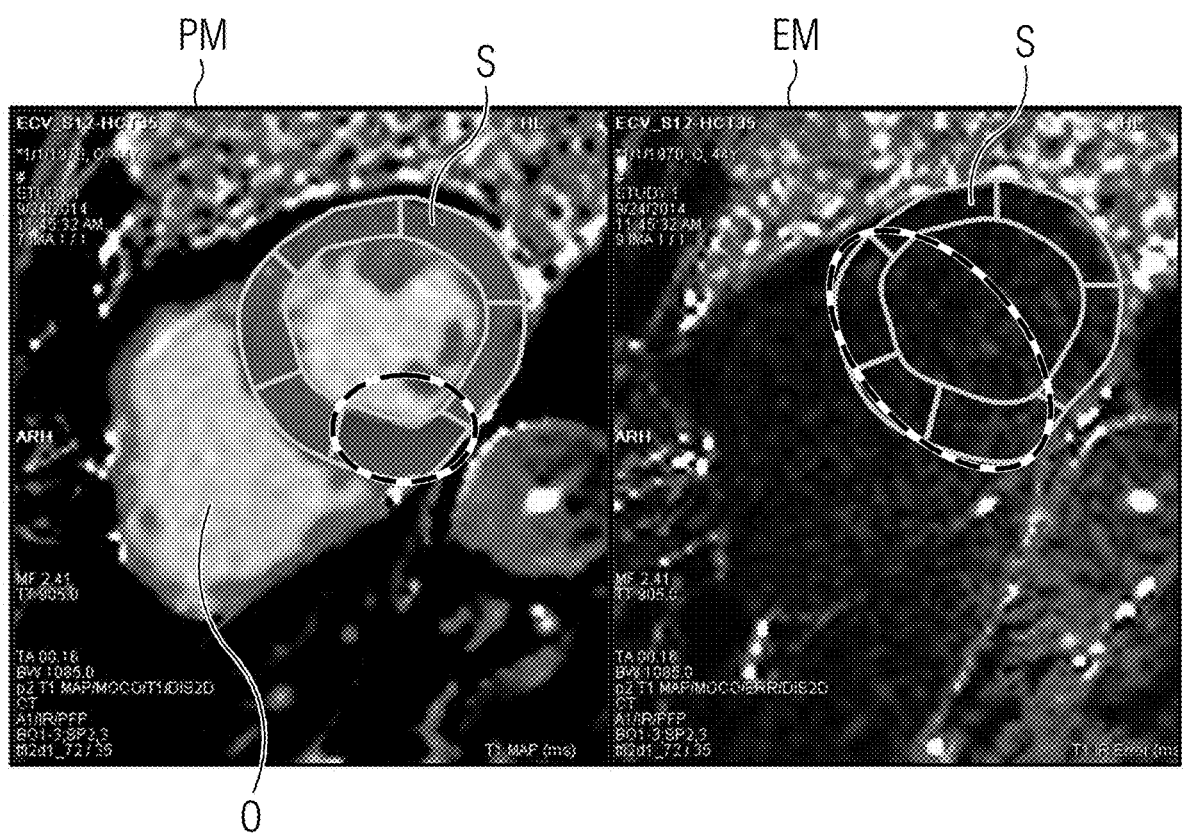
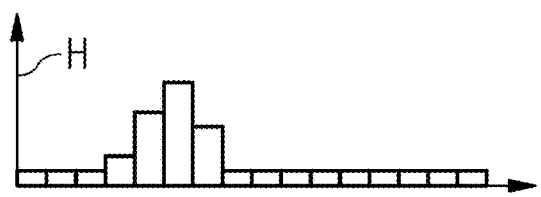

METHOD AND DEVICE FOR ANALYZING ACQUIRED MAGNETIC RESONANCE IMAGES

CROSS REFERENCE TO RELATED APPLICATIONS

This patent application claims priority to European Patent Application No. 18185260.9, filed Jul. 24, 2018, which is incorporated herein by reference in its entirety.

BACKGROUND

Field

The disclosure relates to a method and a device for analyzing acquired magnetic resonance images, in particular for the combined error analysis and generation of inline results for quantitative magnetic resonance parameter mapping.

Related Art

During the generation of quantitative parameter maps, such as e.g. in the course of a T1 mapping of the heart, inline parameter maps are generated. In order to generate the maps, a plurality of images are acquired and registered. A model function is then fitted pixel by pixel, e.g. as part of an inversion recovery 3-parameter fit. The resulting pixel maps are intended to reveal malignant changes in the myocardial tissue. Changes in specific tissue regions can be quantified by manually drawing in target regions (also known as "regions of interest" (ROI)).

A problematic aspect with the prior art approach is that artifacts can occur, e.g. due to respiratory motion or due to variable heart rates, which can distort the results and in the worst case be interpreted as pathological findings. Quality assurance has not been automatically guaranteed to date.

Attempts to address these problems include user checking to monitor the quality of the raw data insofar as the user was able to identify typical distortions in the maps and distinguish these from genuine lesions. All further evaluations had to be carried out offline since an interaction by a user was always necessary there too in order to select the pixels of the ROI that were to be studied (e.g. in the heart tissue or in the blood).

A disadvantage of the conventional systems and methods is that the result of the examination is dependent in practice on the user performing the evaluation, in particular on his or her manual selection of the pixels.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

FIG. 3 shows a representation of an example result of the method according to an exemplary embodiment of the present disclosure.

FIG. 4 shows a representation of another example result of the method according to an exemplary embodiment of the present disclosure.

FIG. 5 shows a representation of another example result of the method according to an exemplary embodiment of the present disclosure.

Figure 1:
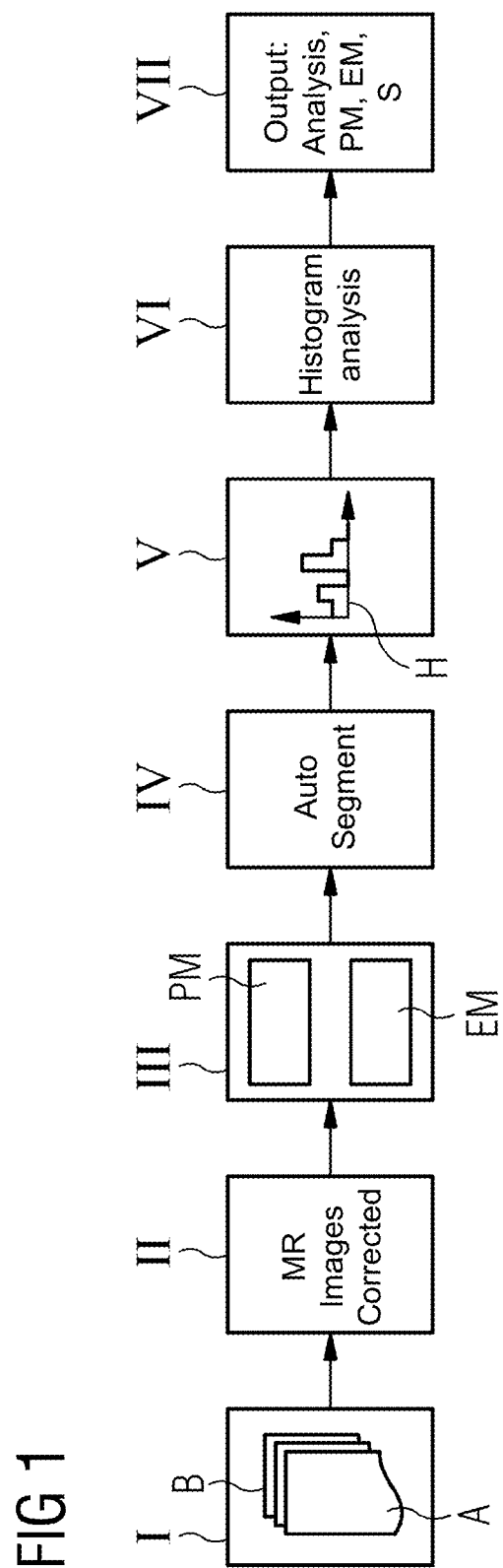
FIG. 1 shows a flowchart of a method according to an exemplary embodiment of the present disclosure.

The exemplary embodiments of the present disclosure will be described with reference to the accompanying drawings. Elements, features and components that are identical, functionally identical and have the same effect are—insofar as is not stated otherwise—respectively provided with the same reference character.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure.

It is an object of the present disclosure to provide a more convenient method and a corresponding device by which the above-described disadvantages are avoided, and in particular, an automated solution is realized so that a comparable quality can be achieved at all times.

The disclosure relates to a method and a device for analyzing acquired magnetic resonance images. In an exemplary embodiment, the method includes a combined error analysis and generation of inline results for quantitative magnetic resonance parameter mapping (MR parameter mapping). A central idea of the present disclosure is in particular to assess the measured mapping data by means of a systematic, automated (inline) evaluation in respect of its quality and at the same time—given satisfactory quality—already generate quantitative results according to a standardized evaluation.

In an exemplary embodiment, the method according to the disclosure for analyzing acquired magnetic resonance images (also referred to as "acquired MR images" for short) includes: Providing an image series, Generating maps, Automatic segmentation, Generating histograms, Analysis, and Output. One or more of these operations may be omitted in aspects of the disclosure. These operations are each discussed in more detail below.

Providing an Image Series

In an exemplary embodiment, the image series includes a number of acquired magnetic resonance images, i.e. images that have been produced by means of an imaging magnetic resonance tomography system. These acquired magnetic resonance images relate to at least one slice of an object, the object usually being a part of a human or animal patient, e.g. an organ. In this process, the acquired magnetic resonance images of the image series have a variation of a contrast-determining acquisition parameter, e.g. a variation of the inversion time in the case of T1 mapping. Images of the image series have therefore been acquired with a constantly changing value for a contrast-determining acquisition parameter. For example, the image series includes a plurality of acquired magnetic resonance images (e.g. T1 contrasts) of a human heart, the same slice through the heart having been imaged every time with longer and longer (or at least different) inversion times.

Conventional protocols for varying the contrast-determining acquisition parameter exist. For example, a value of an acquisition parameter can be continually increased or reduced within a value interval. Further exemplary contrast-determining acquisition parameters are the echo time TE or the T2 preparation duration, a diffusion weighting, a flow weighting, a perfusion or a magnetization transfer.

In an exemplary embodiment, the method can be applied to acquired magnetic resonance images having a single contrast. However, it is also possible to acquire images with a number of contrasts and/or in particular to vary a number of contrast-determining acquisition parameters. The method can then be applied independently to the different contrasts or else to a combination of the contrasts, wherein a model function adapted in the following operations in the process (often also referred to as a "fit function") should of course always be chosen according to the type of variation of the contrast-determining acquisition parameter.

In an exemplary embodiment, the providing operation includes a direct acquisition (or a measurement of quantitative mapping data) by a magnetic resonance tomography system or a providing of previously produced acquired magnetic resonance images from a data store, e.g. a PACS (Picture Archiving and Communication System).

Acquired magnetic resonance images can include individual (two-dimensional) slices. However, the method according to the disclosure can also be applied to 3D data. What is important is that one parameter per function fit (see following remarks) can be quantitatively evaluated from the image series. It is perfectly possible to scan multiple slices, though it is important to ensure that in the further course of the method picture elements having (substantially) identical space coordinates are considered in the individual images. If images from different slices are present in an image series, those images showing the same space coordinates are considered in each case in the further course of the method.

Generating Maps

Maps containing parameter values and errors are generated. To provide a better understanding, these maps are referred to in the following as "parameter maps" and "error maps" since these terms are often used internationally. In an exemplary embodiment, even if the nature of the parameters can basically be chosen freely, inline parameters are preferred. In an exemplary embodiment, the (where appropriate, inline) parameter maps and error maps are generated by fitting picture elements of the acquired magnetic resonance images of the image series. In this context the picture elements for a fit correspond in each case to identical regions of identical motifs of the images of the image series or, as the case may be, identical space coordinates of the object. The picture elements in most cases include individual pixels or pixel groups.

For example, in an image series of a heart, in which the heart is always imaged identically in its shape (e.g. because the images have been registered onto one another), a model function is fitted to consistently identical regions of the imaging of the heart (e.g. the same pixel of the right ventricle). This fitting is achieved by way of the value of the respective pixel (e.g. color or brightness) in the different images of the image series, which value changes from image to image with the variation of the contrast-determining parameter.

In an exemplary embodiment, the model function includes a mathematical function (e.g. a polynomial) having a number of parameters whose values are determined during the fit (modeling) in such a way that the function is able to describe approximately (with a smallest possible deviation: the error) the values of the pixel in question in all images of the image series.

The values of a number of these parameters (a single one or multiple) are reproduced in the parameter map, while the values of the errors are reproduced in the error map. For example, an exponential decay function $e^{(-TE/T2)}$ with the contrast T2 is fitted per pixel over the various images of the image series, the pixel values corresponding in each case to the measured contrast for the echo time TE varied in this example. In this example, TE was the contrast-determining acquisition parameter and the values sorted into the parameter map for the individual pixels are those values for TE which permitted the best fit. The error values of the respective fit are entered in the error map.

In an exemplary embodiment, it is particularly advantageous in this context if there is produced in each case, as a parameter map and as an error map, an image in which the values of the parameters are also entered at the coordinate at which the respective examined image regions (e.g. pixels) of the images of the image series were located. In an exemplary embodiment, if such a fit is now performed for a series of image regions (e.g. pixels), preferably for each image region, there is produced in each case for the parameter map and the error map an image which reproduces the parameter values and errors (error values) in the motif (at the respective position). This classification has the particular advantage that the segmentation (see operation explained below), the scaling of which is based on the acquired magnetic resonance images, can be very easily projected onto the maps.

In an exemplary embodiment, if, for example, the model function for individual pixels has a single parameter, then the parameter map of the above-cited example of a scan of the heart could represent the heart, each pixel in this case reproducing the value of the parameter. Since there is a great probability that the parameter values in the region of the heart differ from the parameter values in the surrounding areas of the heart, the heart will usually be clearly identifiable in a visualization of this parameter map.

The values of a parameter map are therefore values of one or more fit parameters, while the values of an error map are the errors of the corresponding fit. Since there is generally a value and an error for each parameter, it is possible to speak of a parameter map and an "associated" error map if the error map reproduces the error of that parameter whose value is present in the parameter map (the same applies to parameter groups). In an exemplary embodiment, the parameter map and the error map span a 2D space in which the measurement results per pixel or picture element can be represented. All values (of the parameters or errors) can be entered in a single respective map, though it is also possible to generate an individual map for every single parameter (or a group of parameters).

Automatic Segmentation

The acquired magnetic resonance images are segmented. In an exemplary embodiment, the segmentation is done independently of the preceding fit with respect to time, but also sequentially in time. An automatic segmentation of an acquired medical image, e.g. a segmentation into American Heart Association (AHA) segments, is known to the person skilled in the art. The segments relevant to the below-described histograms are generated by the segmentation.

The parameter map(s) and the error map(s) of the segments can now be represented, e.g. in the form of a 2D plot in which a parameter map is displayed next to the associated error map together with a representation of the segmentation in the individual maps (See FIGS. 3-5).

In an exemplary embodiment, alternatively or in addition, the following operations can also be performed:

Generating Histograms

In an exemplary embodiment, after the fit and the segmentation have been performed, histograms of a parameter map and of the associated error map are generated. In an exemplary embodiment, the values of the parameter map and the error values corresponding to the parameter in the associated error map within a segment are incorporated in a respective histogram, the respective values being sorted into bins. In most cases this results (at least in respect of the parameter map) in histograms having an accumulation value which can be different from segment to segment. In an exemplary embodiment, the automatic segmentation makes, for example, assumptions about the topology of a tissue region, such as assumptions about the ring-shaped structure of the left ventricle in the short axis slice.

Analysis

An analysis of the histograms then follows. In the preceding example, a histogram-based analysis of the AHA segments of the parameter maps and error maps would be performed. In an exemplary embodiment, in the analysis, it is determined, based on the histogram, in comparison with reference histograms or reference values, whether an anomaly is present in the respective segment or not. In an exemplary embodiment, statistical analyses of the histograms are preferred. For example, a shift in an accumulation value in a histogram from a normal value to a different value or the forming of a new (further) accumulation value can allow a pathological change or another anomaly to be inferred, e.g. a fraction of the blood in tissue. Preferred embodiments of the analysis will be explained in greater detail below.

Output

In an exemplary embodiment, following the analysis, the results of the analysis are output. Preferably, the parameter maps and the error maps of the segments are presented in this case together with the results of the analysis, e.g. in the form of a 2D plot in which a parameter map is output alongside an error map together with a representation of the segmentation in the individual maps.

A histogram analyzer according to an exemplary embodiment of the disclosure for analyzing acquired magnetic resonance images is configured to conduct an analysis of histograms within the scope of a method of one or more aspects of the disclosure.

In an exemplary embodiment, an analyzer system according to the disclosure for analyzing acquired magnetic resonance images includes:

A data interface configured to receive an image series including a number of acquired magnetic resonance images of a slice of an object, where the acquired magnetic resonance images have a variation of a contrast-determining parameter.

A map generator configured to generate parameter maps and error maps by fitting of picture elements of the acquired magnetic resonance images of a received image series.

A segmentator configured to automatically segment the acquired magnetic resonance images.

A histogram generator configured to generate histograms of the parameter maps and error maps and the histogram.

An output interface configured to visualize the parameter maps and the error maps of the segments, and/or to output the results of the analysis.

A medical system according to the disclosure includes an analyzer system according to one or more embodiments of the disclosure for analyzing acquired magnetic resonance images. In an exemplary embodiment, the medical system includes a diagnostic assessment station or a controller including the analyzer system.

In an exemplary embodiment, one or more of the aforementioned components of the analyzer system can be realized wholly or in part in the form of software modules in a processor of a corresponding analyzer system. In an exemplary embodiment, the analyzer system (or one or more of the components therein) includes processor circuitry that is configured to perform one or more functions and/or operations of the analyzer system. In an exemplary embodiment, the processor circuitry can be configured to execute software of one or more of the software modules to effectuate the operations of the analyzer system. An implementation largely in software has the advantage that control facilities or diagnostic assessment stations already used previously in the prior art can also be easily upgraded by a software update in order to operate in the manner according to the disclosure. In that respect, the object is also achieved by a corresponding computer program product comprising a computer program which can be loaded directly into a device and having program sections for performing all operations of the method according to the disclosure when the program is executed in the device. As well as the computer program, such a computer program product may, where appropriate, include additional constituent parts such as e.g. a set of documentation and/or additional components, including hardware components, such as e.g. hardware keys (dongles, etc.) to allow use of the software.

A computer-readable medium, for example a memory stick, a hard disk, compact disk, solid state memory, volatile or non-volatile memory, or some other portable or permanently installed data carrier on which the program sections of the computer program that can be read in and executed by a computing system or a computer of the device are stored may be used for transporting the computer program product to the device and/or for storing the same on or in the computing system or the device. For this purpose, the computer may include one or more cooperating microprocessors or the like.

In an exemplary embodiment, a number of histograms of a parameter map and an error map are formed. In this context, a histogram includes the information of the corresponding parameter maps and error maps within a segment.

In an exemplary embodiment, the analysis of a histogram for a region of the parameter maps and/or of the error maps is carried out by a comparison with a comparison variable, such as a comparison histogram or a comparison value. In this case, the results are determined from differences between histogram and comparison variable, in that the differences are analyzed based on previously known patterns and/or based on algorithms trained using the principles of machine learning or deep learning.

In an exemplary embodiment, comparison variables are used which are typical of anomalies (e.g. of diseased tissue) or comparison variables which are typical of the normal state (e.g. of healthy tissue). In this regard, a difference is preferably formed between histogram and comparison variable and the result of the difference is examined further.

In an exemplary embodiment, the analysis of a histogram is carried out using mathematical approaches for a spectral analysis. In an exemplary embodiment, supplementary information is taken into account in this case. In an exemplary embodiment, the supplementary information includes details concerning patient characteristics (e.g. BMI or age) or about device characteristics of the device from which the acquired magnetic resonance images originate. For example, an indication pointing to a high BMI could improve an analysis in respect of the fat content.

In an exemplary embodiment, the supplementary information includes value ranges or difference values, such as in respect of T1 in blood, myocardium or fat, so that the relative fractions of these components can be identified. Inferences about the data quality (e.g. a blood contamination) or the clinical findings (e.g. a fat accumulation) can then be made on the basis of the relative fractions.

In an exemplary embodiment, the acquired magnetic resonance images of the image series undergo a correction, such as a motion correction. In an exemplary embodiment, the correction is achieved by an (in particular elastic) registration of the acquired magnetic resonance images of the image series onto one another. The further method is then carried out using corrected (in particular motion-corrected) images. The correction is advantageous, possibly even necessary, if the examined tissue regions are subject to movement. This applies e.g. to the heart and the liver, but also possibly to the head. In an exemplary embodiment, the correction is performed by a corrector 20.

In an exemplary embodiment, it is advantageous if the segmentation is carried out before the acquired magnetic resonance images of the image series are corrected. In an exemplary embodiment, the correction (that is, the registration) is then carried out within the segments. This results in a time saving and frequently also produces an improvement in the quality of the registration. The registration of the acquired images is therefore performed prior to the (in particular pixelwise) parameter fit.

In an exemplary embodiment, the parameters are fitted picture element by picture element in order to generate a parameter map and/or an error map. An inversion recovery 3-parameter fit is preferably performed in the process. As has already been described above, a model function, preferably an exponential function, is preferably fitted pixel by pixel.

In an exemplary embodiment, the automatic segmentation of the acquired magnetic resonance images is performed in accordance with an AHA segment model or according to a machine-learning-or deep-learning-based method. Short-axis slices are preferred in this case. In this regard, the AHA segment model is particularly well suited to the method according to the disclosure, though in principle, the method can also be applied to all tissue regions. The segmentation is preferably performed using the same kernel algorithm as the "InlineVF" or syngo.via ventricular function analysis.

In an exemplary embodiment, the acquired magnetic resonance images have contrasts of the T1 group, in particular T1 pre/post, T2, T2*, ExtraCellular Volume (ECV), diffusion, perfusion, etc. In an exemplary embodiment, there takes place in this case: a variation of the inversion time (e.g. in the case of T1 mapping), a variation of the echo time, of the preparation duration, of the diffusion weighting, of the flow weighting, of the perfusion or of the magnetization transfer.

In an exemplary embodiment, the results of the analysis are output in the form of a two-dimensional plot of parameter values of the parameter map and error values of the error map. In this case, in particular the parameter map and the error map are presented next to each other together with a visualization of the segments that resulted in the segmentation, and are output together with the results of the analysis. With the fastest possible output, the data can already be evaluated sufficiently well soon after the measurement in order e.g. to decide on the need for a rescan, if necessary with modified measurement parameters.

In an exemplary embodiment, a check is carried out within the scope of the analysis for predefined deviation patterns in a segment and a recommendation for a further measurement is output if the deviation pattern is present. In an exemplary embodiment, one or more of the following checks are conducted:

Check whether homogeneously higher values are present in the error map. An SNR problem can then be inferred therefrom. In an exemplary embodiment, a check of the coils is suggested within the scope of the output.

Check whether locally higher values are present according to an anatomical structure. A movement can then be inferred therefrom. In an exemplary embodiment, a better breath control is suggested within the scope of the output.

Check whether locally increased values are present independently of an anatomical structure. A banding can then be inferred therefrom. In an exemplary embodiment, a patient-specific shim is suggested within the scope of the output.

Check whether there is a strong variability in the parameter map (in particular for T1 contrast), though low values are present in the error map. A fat accumulation can then be inferred therefrom. In an exemplary embodiment, Dixon is suggested within the scope of the output. If e.g. a large fat content is identified, an additional measurement for fat is suggested.

Causes of errors can be differentiated and specifically addressed based on the value distributions of the pixels in a segment.

The method can be applied in principle to all mapping methods or, as the case may be, to all acquired MR images that permit an automatic tissue segmentation and include a parameter fit in respect of a measured characteristic variable such as e.g. T1, T2, T2*, diffusion, perfusion, etc.

The segment-based evaluation in itself reliably furnishes information about pathological changes (provided the data quality is sufficient). The detection of the error patterns can be particularly efficiently implemented through the use of machine learning or deep learning.

Owing to the automatic segmentation, results from different relevant parameters (e.g. T1, T2) can be merged in a common inline evaluation, where appropriate on co-registered data, and in this way the diagnostic value of the measurement can be further increased.

Compared with conventional systems and methods, the proposed inclusion of error maps, automatic inline segmentation, and a structured evaluation advantageously permits a faster assessment of the measurement results. This firstly enables a response already during the examination in the form of a repetition of the measurement or an initiation of additional measurements on the basis of the quantitative results, e.g. a fat-water separation measurement if very low T1 values are measured, in order to detect fat accumulations, or a rescan after advanced shim adjustment if off-resonance artifacts are visible in the error maps.

In this way, the frequency of non-diagnostic measurements is reduced and the reliability of the diagnosis increased. A further consequence of the inline evaluation is that time-consuming offline evaluations can be avoided or at least shortened.

Owing to the editing of the pixel map results in the form of results classified as reliable by means of the error maps as histograms per segment/slice, the data is already available in a suitable format in order to apply more complex statistical methods such as pattern recognition or to feed the histogram results together with the normal value distribution into a learning algorithm, which then detects e.g. the typical value distributions for specific disease symptoms.

The standardized inline segmentation and evaluation furthermore enables the measurement results for different parameters, such as e.g. T1 pre/post, ECV, T2, perfusion, etc., also to be merged already inline in the evaluation and e.g. to include the same in multiparametric cluster analyses for classifying tissue changes.

FIG. 1 shows a flowchart of a method according to an exemplary embodiment of the disclosure for analyzing acquired magnetic resonance images A.

In operation I, an image series B is provided comprising a number of acquired magnetic resonance images A of a slice of an object, for example a heart (see in this regard e.g. FIGS. 2 to 5), the acquired magnetic resonance images A having a variation of a contrast-determining acquisition parameter. In the case of e.g. acquired magnetic resonance images A such as those that served as a basis for FIGS. 3 to 5 and represented a T1 contrast, the contrast-determining acquisition parameter can be the inversion time, which is varied in ascending order (toward longer inversion times) or descending order (toward shorter inversion times) within a time interval.

In operation II, the acquired magnetic resonance images A of the image series B are corrected on account of the fact that e.g. a heart beats constantly during the scan. In this case, the acquired magnetic resonance images A of the image series B can for example be registered onto one another, one of the acquired magnetic resonance images A being specified as a reference image and the object O (e.g. the heart) being registered onto the reference image in all other relevant acquired magnetic resonance images A. The further method is then carried out using the corrected magnetic resonance images A. Theoretically, this operation can be omitted if the acquired images being worked with are already ideal.

In operation III, a parameter map PM and an error map EM are generated. In the process, a model function is fitted e.g. to the values of individual pixels of the images, the pixels in each case being located at the same image coordinates (and consequently in each case showing the same regions of the object, which, however, have been acquired using constantly varying contrast-determining acquisition parameters). The model function includes at least one parameter, the value of which is varied until the model function represents a good reflection of the values of the pixels. The parameter value finally selected is entered in the parameter map PM (preferably at the corresponding image coordinate of a 2D plot) and the error value of the model function is entered in an error map EM (preferably likewise at the corresponding image coordinate of a 2D plot).

In operation IV, an automatic segmentation of the acquired magnetic resonance images A is performed. If the object is a heart, the segmentation of the left ventricle may appear for example as shown in FIGS. 3 to 5.

In operation V, histograms H of the parameter map PM and the error map EM are generated. In the process, the parameter values P of the parameter map PM within a segment are in this case entered in a histogram and the error values E of the error map EM are entered in a different histogram (see e.g. FIGS. 3 to 5).

In operation VI, an analysis of the histograms is carried out (see e.g. description relating to FIGS. 3 to 5).

In operation VII, the results of the analysis are output together with a visualization of the parameter map PM and the error map EM and the segments S.

Figure 2:
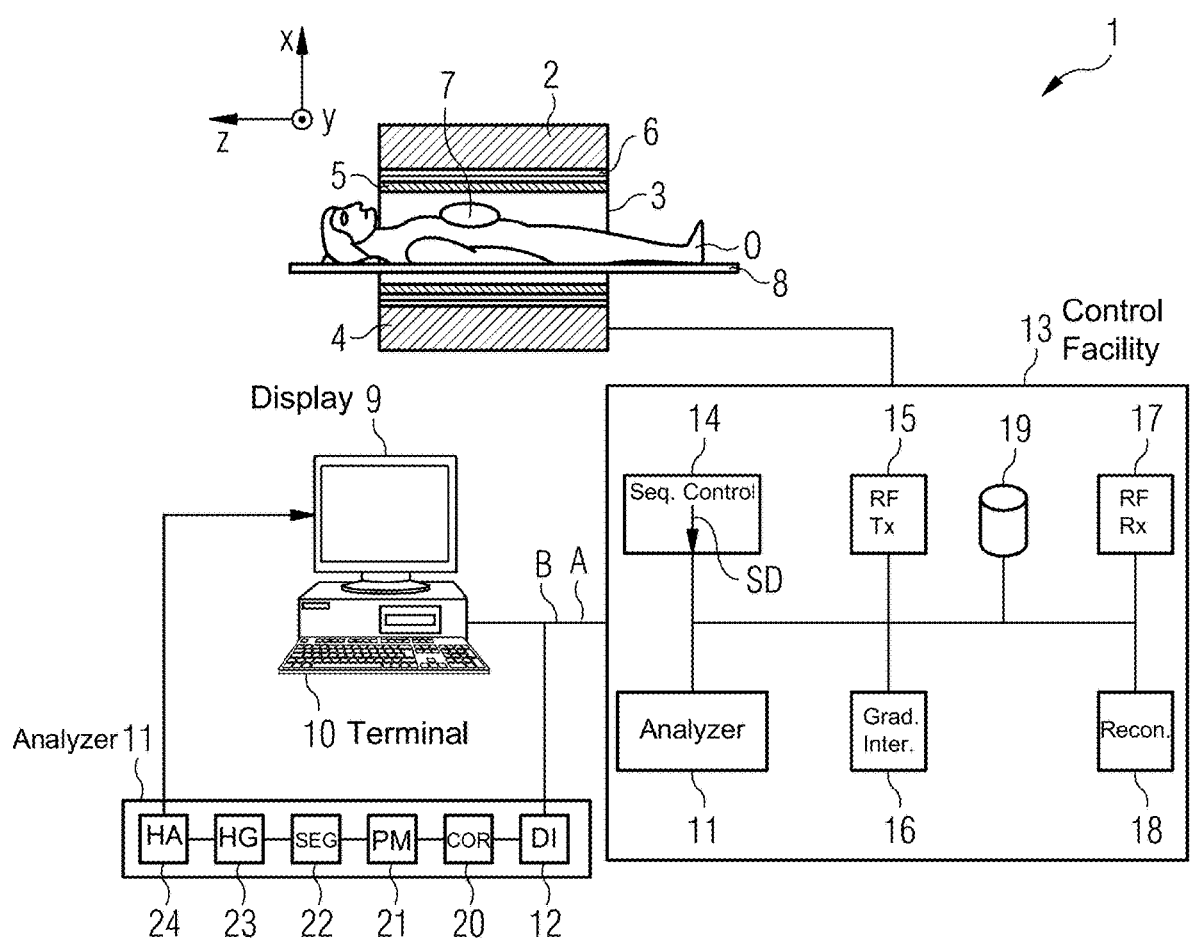
FIG. 2 shows a schematic representation of a magnetic resonance tomography system according to an exemplary embodiment of the present disclosure.

FIG. 2 shows a rough schematic representation of a magnetic resonance tomography system 1 according to an exemplary embodiment. In an exemplary embodiment, the system 1 includes a magnetic resonance scanner 2 having an examination chamber 3 or patient tunnel in which a patient or test volunteer whose body contains the actual examination object O (e.g. the heart or liver) is positioned on a couch 8.

The magnetic resonance scanner 2 is equipped in the conventional manner with a basic field magnet system 4, a gradient system 6, and also an RF transmit antenna system 5 and an RF receive antenna system 7. In the exemplary embodiment shown, the RF transmit antenna system 5 is a whole-body coil permanently installed in the magnetic resonance scanner 2. The basic field magnet system 4 is in this case embodied in the conventional manner such that it generates a basic magnetic field in the longitudinal direction of the patient, i.e. along the longitudinal axis of the magnetic resonance scanner 2 extending in the z-direction. The gradient system 6 includes individually drivable gradient coils in the conventional manner in order to enable gradients to be switched independently of one another in the x-, y- or z-direction. The magnetic resonance scanner 2 also contains shim coils (not shown), which can be embodied in the conventional manner.

The magnetic resonance tomography system shown in FIG. 2 is a whole-body system having a patient tunnel into which a patient can be fully introduced. In principle, however, the disclosure can also be used on other magnetic resonance tomography systems, e.g. having a C-shaped housing with side access opening. The only essential point is that corresponding acquired images of the examination object O can be produced.

In an exemplary embodiment, the magnetic resonance tomography system 1 additionally includes a central control facility 13 which is used for controlling the MR system 1. The central control facility 13 includes a sequence controller 14. In an exemplary embodiment, the sequence controller 14 is configured to control the succession of radiofrequency pulses (RF pulses) and gradient pulses as a function of a chosen pulse sequence or a succession of multiple pulse sequences for scanning a plurality of slices in a volume region of interest of the examination object within a measurement session. Such a pulse sequence can be specified and parameterized for example within a measurement or control protocol. Typically, various control protocols for different measurements or measurement sessions are stored in a memory 19 and can be selected by an operator (and possibly modified if necessary) and then used for performing the measurement.

In order to output the individual RF pulses of a pulse sequence, the central control facility 13 has a radiofrequency transmit facility 15 which generates the RF pulses, amplifies them and feeds them into the RF transmit antenna system 5 via a suitable interface (not shown in detail). To control the gradient coils of the gradient system 6 in order to switch the gradient pulses appropriately in accordance with the specified pulse sequence, the control facility 13 has a gradient system interface 16. The diffusion gradient pulses and spoiler gradient pulses could be applied via the gradient system interface 16. The sequence controller 14 communicates in a suitable manner, e.g. by transmitting sequence control data SD, with the radiofrequency transmit facility 15 and the gradient system interface 16 in order to execute the pulse sequence.

The acquisition of suitable raw data by irradiation with RF pulses and generation of gradient fields, and to reconstruct magnetic resonance tomography images ("acquired magnetic resonance images" A) therefrom, is generally known to the person skilled in the art and is discussion of such is therefore omitted for brevity. Similarly, a vast range of measurement sequences, such as e.g. EPI measurement sequences or other measurement sequences for generating diffusion-weighted images, are generally known to the person skilled in the art.

In an exemplary embodiment, the control facility 13 also includes a radiofrequency receive facility 17 (likewise communicating in a suitable manner with the sequence controller 14) in order to receive magnetic resonance signals in a coordinated fashion by means of the RF receive antenna system 7 within the readout windows specified by the pulse sequence and in this way to acquire the raw data.

In an exemplary embodiment, a reconstructor 18 is configured to accept the acquired raw data in this case and reconstruct magnetic resonance images A therefrom. This reconstruction, too, is usually performed on the basis of parameters that can be specified in the respective measurement or control protocol P. This image data can then be stored in a memory 19, for example.

The acquisition of suitable raw data by irradiation with RF pulses and switching of gradient pulses, and the reconstructing of magnetic resonance images A therefrom, is generally known to the person skilled in the art and discussion of such is therefore omitted for brevity. In an exemplary embodiment, the magnetic resonance tomography system 1 according to the disclosure and in particular the control facility 13 can additionally include a plurality of further components, not shown specifically here, but typically present on such systems, such as, for example, a network interface in order to connect the overall system to a network, and to enable raw data and/or image data, but also other data, such as, for example, patient-relevant data or control protocols, to be exchanged. In an exemplary embodiment, the control facility 13 (and/or one or more component comprised therein) includes processor circuitry that is configured to perform one or more functions/operations of the control facility (or one or more respective functions/operations of the corresponding component).

In an exemplary embodiment, the operator control of the central control facility 13 is possible by way of a terminal 10. In an exemplary embodiment, the terminal 10 includes an input and a display 9, via which the entire magnetic resonance tomography system 1 can therefore also be controlled by an operator. Acquired magnetic resonance images A can also be displayed on the display 9, and measurements can be planned and started by means of the input, where appropriate in combination with the display 9, and in particular a diagnostic assessment can also be carried out. In an exemplary embodiment, the terminal 10 includes processor circuitry that is configured to perform one or more functions/operations of the terminal 10. In an exemplary embodiment, the terminal 10 is a special-purpose computer that includes one or more software programs installed therein (and/or accessible by the computer), that when executed by one or more processors of the computer, performs the operations of the terminal 10.

In an exemplary embodiment, the control facility 13 includes an analyzer 11 according to the disclosure, though this may also be disposed in the terminal 10, or arranged on an external diagnostic assessment station. In an exemplary embodiment, the terminal 10 may additionally or alternatively be configured to serve as a diagnostic assessment station 10. In an exemplary embodiment, the analyzer 11 indicated in the control facility 13 has the same internal structure (i.e. includes components 12, 20, 21, 22, 23, and/or 24) as that shown on the terminal 10, which is described in more detail below.

In an exemplary embodiment, the analyzer 11 for analyzing acquired magnetic resonance images A includes:

A data interface 12 configured to receive an image series B comprising a number of acquired magnetic resonance images A of a slice of an object O. The acquired magnetic resonance images A should in this case have a variation of a contrast-determining acquisition parameter. The image series B is in this instance sent by the control facility 13 and includes the reconstructed magnetic resonance images A.

A corrector 20 configured to correct the acquired magnetic resonance images A. With regard to the operation of the corrector 20 and the operation of the following components, reference is also made to the description in relation to FIG. 1.

A map generator 21 configured to generate a parameter map PM and an error map EM by fitting picture elements of the acquired magnetic resonance images A of the received image series B.

A segmentator 22 configured to automatically segment the acquired magnetic resonance images (A).

A histogram generator 23 configured to generate histograms H of the parameter map PM and the error map EM.

A histogram analyzer 24 configured to analyze the histograms H.

The display 9 of the terminal 10 is used in this case as the output interface 9.

FIGS. 3 to 5 illustrate example outputs of the analyzer 11 according to exemplary embodiments.

FIG. 3 shows a representation of an example result of the method according to an embodiment of the disclosure. Here, the parameter values of a parameter map PM are shown on the left, and the error values of an error map EM on the right. In this case, the parameter map PM and the error map EM have the same image format as the originally acquired magnetic resonance images A. What is shown here is a heart in which the left ventricle in this case represents the region of interest. This left ventricle has been segmented in the image, resulting in six segments S which are arranged approximately in the shape of a circle (for clarity of illustration reasons, only one of the segments S is labeled with a reference sign). In the left-hand image, a region of special parameter values P stands out which forms a possible clinically relevant structure. Shown below the left-hand image is a histogram H which reproduces the parameter values of the lowest segment S. Two accumulation values are clearly to be seen, firstly the background (left accumulation value) and secondly for the special parameter values P (right accumulation value). This could be an indication of the presence of clinical findings. An analysis would identify the second accumulation value, compare this e.g. with reference values and by this means arrive at the possible clinical findings.

In this example, however, upon consideration of the right-hand image (error map EM), special error values E are clearly revealed in the lowest segment S (and also in the adjacent segments on the left thereof). If the histogram H of the error values (bottom right) associated with the lowest segment S is considered, then an accumulation value of extremely high errors is evident. Here, the accumulation value of the error values would be recognized by the analysis and in this case a check of the trigger would be suggested.

FIG. 4 shows a representation of another example result of the method according to an embodiment of the disclosure.

The left side (parameter map PM) is identical to the left side of FIG. 3. No special error values reveal themselves on the right side (error map EM). This is also clearly apparent in the histogram H at bottom right.

In this case, a possible presence of clinical findings would be recognized on the part of the analysis (by the right-hand accumulation value of the histogram H at bottom left) and a corresponding message would be output.

FIG. 5 shows a representation of a further example result of the method according to an exemplary embodiment of the disclosure. Here, neither the left side (parameter map PM) nor the right side (error map EM) reveal special error values or special parameter values P. Accordingly, the histograms H at bottom left and right reveal no special accumulation values (the plotted accumulation values stand for the normal pixel values).

In conclusion, it is pointed out once again that the methods described in detail in the foregoing as well as the illustrated magnetic resonance tomography system 1 are simply exemplary embodiments which may be modified in the most diverse ways by the person skilled in the art without leaving the scope of the disclosure. Furthermore, the use of the indefinite articles "a" or "an" does not exclude the possibility that the features in question may also be present more than once. Similarly, the terms "unit" and "module" do not rule out the possibility that the components in question consist of a plurality of cooperating subcomponents, which if necessary may also be distributed in space.

Conclusion

The aforementioned description of the specific embodiments will so fully reveal the general nature of the disclosure that others can, by applying knowledge within the skill of the art, readily modify and/or adapt for various applications such specific embodiments, without undue experimentation, and without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact results from computers, processors, controllers, or other devices executing the firmware, software, routines, instructions, etc. Further, any of the implementation variations may be carried out by a general purpose computer.

For the purposes of this discussion, the term "processor circuitry" shall be understood to be circuit(s), processor(s), logic, or a combination thereof. A circuit includes an analog circuit, a digital circuit, state machine logic, programmable processing circuit, other structural electronic hardware, or a combination thereof. A processor includes a microprocessor, a digital signal processor (DSP), central processing unit (CPU), application-specific instruction set processor (ASIP), graphics and/or image processor, multi-core processor, or other hardware processor. The processor may be "hard-coded" with instructions to perform corresponding function(s) according to aspects described herein. Alternatively, the processor may access an internal and/or external memory to retrieve instructions stored in the memory, which when executed by the processor, perform the corresponding function(s) associated with the processor, and/or one or more functions and/or operations related to the operation of a component having the processor included therein.

In one or more of the exemplary embodiments described herein, the memory is any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM). The memory can be non-removable, removable, or a combination of both.

The invention claimed is:

1. A method for analyzing acquired magnetic resonance images, comprising:
providing an image series including a plurality of acquired magnetic resonance images of a slice of an object, the plurality of acquired magnetic resonance images having a variation of a contrast-determining acquisition parameter;

fitting picture elements of the plurality of acquired magnetic resonance images of the image series to generate a parameter map and an error map;

automatically segmenting the plurality of acquired magnetic resonance images to generate image segments;

generating histograms, based on the image segments, of the parameter map and the error map, wherein a histogram of the generated histograms includes information of the parameter map and error map within a corresponding one of the image segments; and analyzing the histograms to: generate an output of analysis results and/or generate a visualization including the parameter map, the error map, and the image segments.

2. The method as claimed in claim 1, wherein the analysis of the histograms for corresponding regions of the parameter maps and/or the error maps comprises comparing each of the histograms with a corresponding comparison variable, the analysis results being determined from differences between the histograms and the corresponding comparison variables, wherein the differences are analyzed based on previously known patterns and/or based on one or more algorithms trained with machine learning.

3. The method as claimed in claim 1, wherein the analysis of the histograms is based on one or more mathematical approaches for a spectral analysis using supplementary information.

4. The method as claimed in claim 1, further comprising registering the magnetic resonance images within the image segments onto one another to motion correct the segmented magnetic resonance images to generate corrected image segments, wherein the picture elements of the corrected image segments are fitted to generate the parameter map and the error map.

5. The method as claimed in claim 1, wherein generation of the parameter map and the error map comprises fitting a model function to the picture elements in a picture element by picture element process.

6. The method as claimed in claim 5, wherein the model function is an inversion recovery 3-parameter fit.

7. The method as claimed in claim 5, wherein the model function is an exponential function that is fit pixel by pixel to the picture elements of the plurality of acquired magnetic resonance images.

8. The method as claimed in claim 1, wherein the automatic segmentation of the plurality of acquired magnetic resonance images is performed in accordance with an American Heart Association (AHA) segment model or according to a machine-learning-based method or a deep-learning-based method.

9. The method as claimed in claim 1, wherein the plurality of acquired magnetic resonance images include contrasts of a group of contrasts including T1 contrast, T2 contrast, T2* contrast, ExtraCellular Volume (ECV) contrast, diffusion contrast, and perfusion contrast.

10. The method as claimed in claim 9, wherein the plurality of acquired magnetic resonance images have a variation of: inversion time, echo time, preparation duration, diffusion weighting, flow weighting, perfusion, or magnetization transfer.

11. The method as claimed in claim 1, wherein the analysis results are output in the form of a two-dimensional plot of parameter values of the parameter map and error values of the error map.

12. The method as claimed in claim 11, wherein the parameter map and the error map are provided together and next to each other in the output with a visualization of the image segments together with the analysis results.

13. The method as claimed in claim 1, wherein analyzing the histograms comprises performing a check for predefined deviation patterns in corresponding ones of the image segments and providing a recommendation for a further measurement if a deviation pattern of the predetermined deviation patterns is present.

14. The method as claimed in claim 13, wherein performing the check comprises one or more of:

checking whether homogeneously higher values are present in the error map and inferring a signal-to-noise (SNR) problem therefrom, the output including a suggestion to check coils of a magnetic resonance device that provides the magnetic resonance images;

checking whether locally higher values according to an anatomical structure are present and inferring a movement therefrom, the output including a suggestion for an improved breath control;

checking whether locally increased values are present independently of an anatomical structure and inferring a banding therefrom, the output including a suggestion for a patient-specific shim; and checking whether a strong variability in the parameter map is present with low values present in the error map, and inferring a fat accumulation therefrom, the output including a suggestion for Dixon.

15. A non-transitory computer program product comprising a computer program which is loadable directly into a memory of a computer medical system and includes program sections configured to perform the method as claimed in claim 1 when the computer program is executed by one or more processors of the computing medical system.

16. A non-transitory computer-readable medium on which are stored program sections that can be read in and executed by a computer to cause the computer to perform the method as claimed in claim 1.

17. An analyzer for analyzing acquired magnetic resonance images, comprising:

a data interface configured to receive an image series including a plurality of acquired magnetic resonance images of a slice of an object, the plurality of acquired magnetic resonance images having a variation of a contrast-determining acquisition parameter;

a map generator configured fit picture elements of the magnetic resonance images of a received image series to generate a parameter map and an error map;

a segmentator configured to automatically segment the plurality of acquired magnetic resonance images to generate image segments;

a histogram generator configured to generate histograms, based on the image segments, of the parameter map and the error map, wherein a histogram of the generated histograms includes information of the parameter map and error map within a corresponding one of the image segments; and an output interface configured to: generate a visualized output of the parameter map and the error map of the image segments, and/or output the results of the analysis.

18. The analyzer as claimed in claim 17, further comprising a corrector that is configured to correct the image segments of the plurality of acquired magnetic resonance images to generate corrected image segments, wherein the histogram generator is configured to generate the histograms based on the corrected image segments.

19. A magnetic resonance tomography system comprising:
- a magnetic resonance scanner configured to generate an image series including a plurality of acquired magnetic resonance images; and
- a diagnostic assessment station or a control facility that includes the analyzer as claimed in claim 17 that is configured to analyze the plurality of acquired magnetic resonance images.

\* \* \* \* \*